US00PP34056P2

(12) United States Plant Patent
Beekenkamp

(10) Patent No.: US PP34,056 P2
(45) Date of Patent: Mar. 22, 2022

(54) ***DAHLIA* PLANT NAMED 'BKDAMPI'**

(50) Latin Name: *Dahlia hybrida*
Varietal Denomination: BKDAMPI

(71) Applicant: BEEKENKAMP PLANTS B.V., Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/346,281

(22) Filed: Jun. 13, 2021

(51) Int. Cl.
*A01H 5/02* (2018.01)
*A01H 6/14* (2018.01)

(52) U.S. Cl.
USPC ..... Plt./321
CPC ..... *A01H 6/144* (2018.05); *A01H 5/02* (2013.01)

(58) Field of Classification Search
USPC ..... Plt./321
See application file for complete search history.

*Primary Examiner* — Susan McCormick Ewoldt
(74) *Attorney, Agent, or Firm* — C. Anne Whealy

(57) ABSTRACT

A new and distinct cultivar of *Dahlia* plant named 'BKDAMPI', characterized by its upright to somewhat outwardly spreading and sturdy plant habit; moderately vigorous growth habit; freely branching habit; dense and bushy growth habit; dark green-colored leaves; freely flowering habit; large, decorative type inflorescences with purplish pink-colored ray florets; and good garden performance.

2 Drawing Sheets

Figure 1:
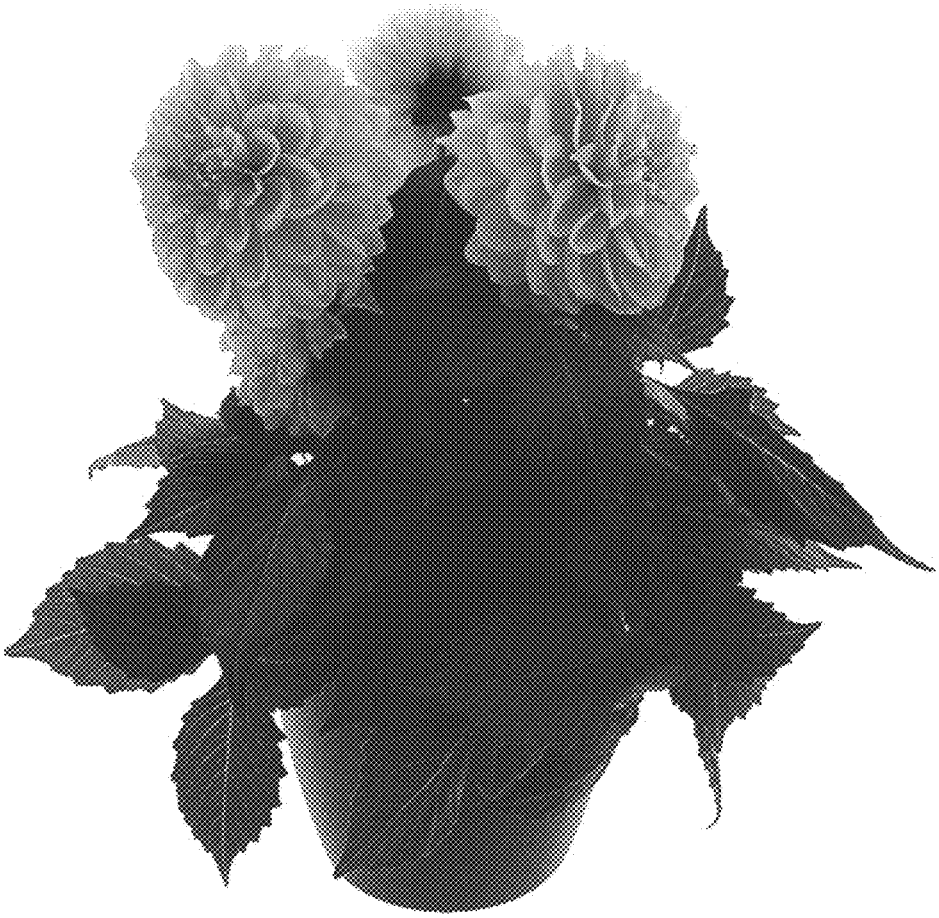

Botanical designation: *Dahlia hybrida.*
Cultivar denomination: 'BKDAMPI'.

STATEMENT REGARDING PRIOR DISCLOSURES BY INVENTOR/APPLICANT and ASSIGNEE

An European Community Plant Breeder's Rights application for the instant plant was filed by the Applicant/Assignee of the instant application, Beekenkamp Plants B.V. of Maasdijk, The Netherlands on Oct. 1, 2020, application number 2020/2422. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Dahlia* plant, botanically known as *Dahlia hybrida* and hereinafter referred to by the name 'BKDAMPI'.

The new *Dahlia* plant is a product of a planned breeding program conducted by the Inventor in Maasdijk, The Netherlands. The objective of the breeding program is to create new freely branching container *Dahlia* plants with large inflorescences and attractive ray floret coloration.

The new *Dahlia* plant originated from an open-pollination in September, 2014 in Maasdijk, The Netherlands of a proprietary selection of *Dahlia hybrida* identified as code number 2007-0120-2, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Maasdijk, The Netherlands in April, 2015.

Asexual reproduction of the new *Dahlia* plant by terminal cuttings in a controlled greenhouse environment in Maasdijk, The Netherlands since June, 2015 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMPI'. These characteristics in combination distinguish 'BKDAMPI' as a new and distinct *Dahlia* plant:

1. Upright to somewhat outwardly spreading and sturdy plant habit.
2. Moderately vigorous growth habit.
3. Freely branching habit; dense and bushy growth habit.
4. Dark green-colored leaves.
5. Freely flowering habit.
6. Large, decorative type inflorescences with purplish pink-colored ray florets.
7. Good garden performance.

Plants of the new *Dahlia* differ primarily from plants of the female parent selection in inflorescence size as plants of the new *Dahlia* have larger inflorescences than plants of the female parent selection. In addition, inflorescences of plants of the new *Dahlia* are more outwardly facing than and not as upright as inflorescences of plants of the female parent selection.

Plants of the new *Dahlia* can be compared to plants of *Dahlia variabilis* 'Daparos', disclosed in U.S. Plant Pat. No. 11,560. In side-by-side comparisons, plants of the new *Dahlia* differ primarily from plants of 'Daparos' in inflorescence size as plants of the new *Dahlia* have larger inflorescences than plants of 'Daparos'. In addition, inflorescences of plants of the new *Dahlia* are more outwardly facing than and not as upright as inflorescences of plants of 'Daparos'.

Plants of the new *Dahlia* can be compared to plants of *Dahlia variabilis* 'Rio Grande', disclosed in U.S. Plant Pat. No. 12,797. In side-by-side comparisons, plants of the new *Dahlia* differ primarily from plants of 'Rio Grande' in inflorescence size as plants of the new *Dahlia* have larger inflorescences than plants of 'Rio Grande'. In addition, inflorescences of plants of the new *Dahlia* are more outwardly facing than and not as upright as inflorescences of plants of 'Rio Grande'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet (FIG. 1) is a side perspective view of a typical flowering plant of 'BKDAMPI' grown in a container.

Figure 2:
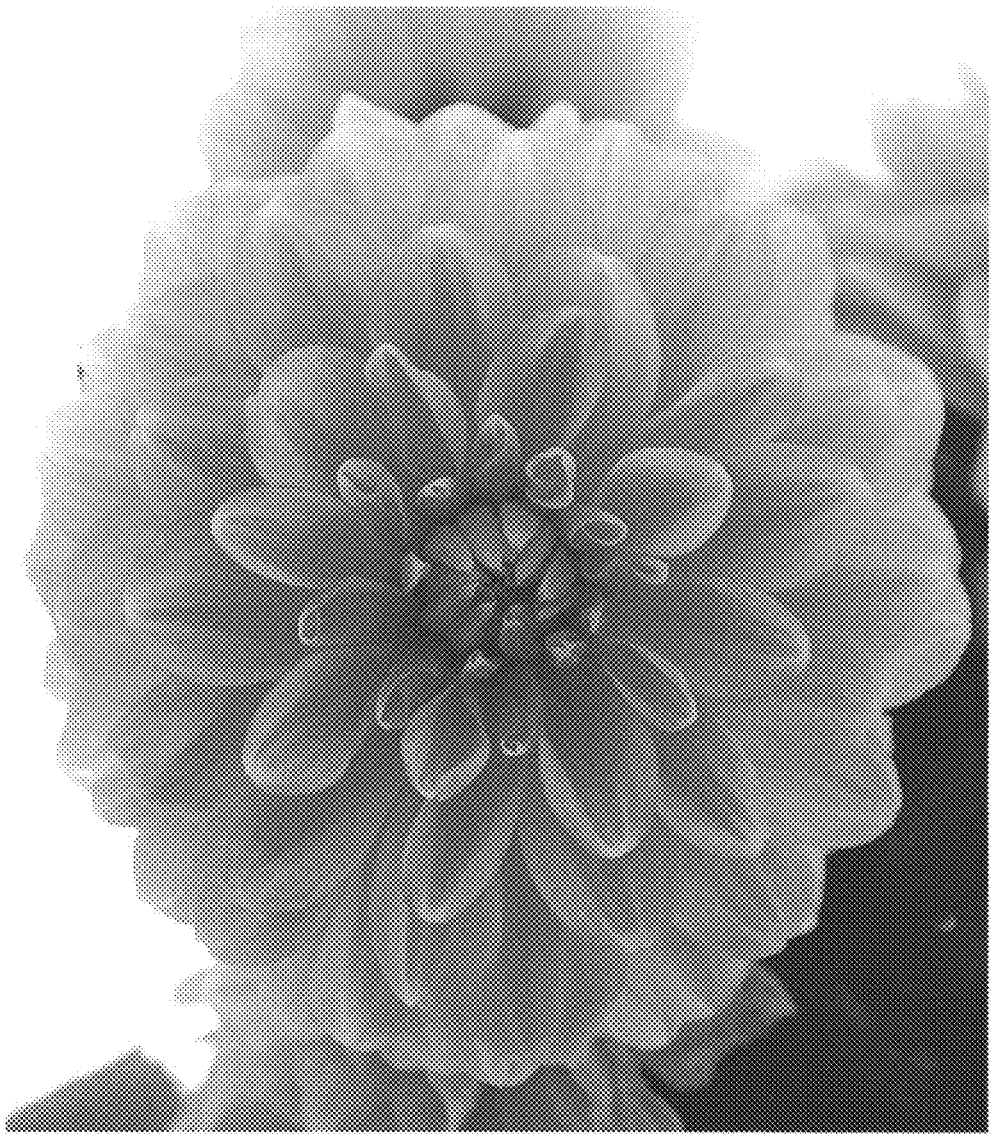

The photograph on the second sheet (FIG. 2) is a close-up view of a typical inflorescence of 'BKDAMPI'.

DETAILED BOTANICAL DESCRIPTION

The aforementioned photographs and the following observations and measurements describe plants grown during the autumn and winter in 11-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were nine weeks from planting rooted cuttings when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDAMPI'.

Parentage:

*Female, or seed, parent*.—Proprietary selection of *Dahlia hybrida* identified as code number 2007-0120-2, not patented.

*Male, or pollen, parent*.—Unknown selection of *Dahlia hybrida*, not patented.

Propagation:

*Type*.—By terminal cuttings.

*Time to initiate roots, summer*.—About 16 days at temperatures ranging from 18° C. to 21° C.

*Time to initiate roots, winter*.—About 19 days at temperatures about 21° C.

*Time to produce a rooted young plant, summer*.—About 21 days at temperatures ranging from 18° C. to 21° C.

*Time to produce a rooted young plant, winter*.—About 23 days at temperatures ranging from 19° C. to 21° C.

*Root description*.—Medium in thickness, fibrous; typically creamy white to light brown in color, actual color of the roots is dependent on substrate composition, water quality, fertilizers, substrate temperature and physiological age of roots; tuber development has not been observed on plants of the new *Dahlia*.

*Rooting habit*.—Moderately freely branching; medium density.

Plant description:

*Plant and growth habit*.—Upright to somewhat outwardly spreading plant habit; overall plant shape, roughly flattened globular with inflorescences held above the foliar plane on strong peduncles; freely basal branching habit with about three primary branches each with about two secondary branches developing per plant; bushy and dense growth habit; pinching is not required but will improve branching habit; moderately vigorous growth habit and moderate growth rate.

*Plant height, soil level to top of foliar plane*.—About 14.3 cm.

*Plant height, soil level to top of floral plane*.—About 20.3 cm.

*Plant diameter or spread*.—About 22.3 cm.

*Lateral branches*.—Length: About 8.3 cm. Diameter: About 6 mm. Internode length: About 2.1 cm. Aspect: Primary branches are about 20° from vertical; secondary branches are about 25° from primary branch axis. Strength: Moderately strong to strong. Texture and luster: Smooth, glabrous; moderately glossy. Color, developing: Close to 144A. Color, developed: Close to 146A.

Leaf & leaflet description:

*Arrangement*.—Leaves opposite; compound with typically five leaflets.

*Length, leaves*.—About 13.8 cm.

*Width, leaves*.—About 13.4 cm.

*Length, terminal leaflets*.—About 7.4 cm.

*Width, terminal leaflets*.—About 3.9 cm.

*Length, lateral leaflets*.—About 6.6 cm.

*Width, lateral leaflets*.—About 3.5 cm.

*Shape, leaves*.—Broadly ovate in outline.

*Shape, leaflets*.—Ovate to elliptic.

*Apex, leaflets*.—Apiculate.

*Base, leaflets*.—Attenuate.

*Margin, leaflets*.—Coarsely serrate to dentate.

*Venation pattern, leaflets*.—Pinnate.

*Texture and luster, upper surface, leaflets*.—Mostly smooth, glabrous with main vein, moderately pubescent; not rugose; moderately glossy.

*Texture and luster, lower surface, leaflets*.—Mostly smooth, glabrous with venation, sparsely to moderately pubescent; slightly rugose; slightly glossy.

*Color*.—Developing leaflets, upper surface: Close to between 137A and 141A. Developing leaflets, lower surface: Close to between 146A and 147B. Fully expanded leaflets, upper surface: Close to between NN137A and 147A; venation, close to 146B. Fully expanded leaflets, lower surface: Close to 191A; venation, close to 146B.

*Petioles*.—Length, leaves: About 3.1 cm. Diameter, leaves: About 3 mm by 4 mm. Strength, leaves: Moderately strong. Texture and luster, leaves, upper and lower surfaces: Smooth, glabrous; glossy. Color, leaves, upper surface: Close to 199A; towards the margins, close to 146A. Color, leaves, lower surface: Close to 146A.

Inflorescence description:

*Appearance and arrangement*.—Decorative type inflorescences with ray and disc florets forming acropetally on a receptacle; inflorescences positioned above and beyond the foliar plane on strong peduncles; inflorescences face mostly outwardly; freely flowering habit with about 18 developing and fully developed inflorescences per plant at one time.

*Fragrance*.—None detected.

*Flowering response and flowering period*.—Early flowering habit, plants begin flowering about 52 days after planting; plants flower continuously during the autumn into the winter in The Netherlands.

*Post-production longevity*.—Inflorescences maintain good substance for about ten days on the plant; inflorescences persistent.

*Inflorescence buds*.—Height: About 9 mm. Diameter: About 2.1 cm. Shape: Flattened globular; involucral bracts slightly reflexed. Texture and luster: Smooth, glabrous; glossy. Color: Close to 143B; towards the base, close to 143A; involucral bracts, close to NN137A.

*Inflorescence size*.—Diameter: About 9.1 cm. Depth (height): About 6.8 cm. Disc diameter: About 1.2 cm; typically inconspicuous.

*Receptacles*.—Height: About 5 mm. Diameter: About 9 mm. Shape: Ovate. Color: Close to 145A.

*Ray florets*.—Quantity per inflorescence and arrangement: About 120 arranged in about eight whorls. Length: About 4.2 cm. Width: About 2.1 cm. Shape: Obovate; concave. Apex: Broadly acute. Base: Attenuate. Margin: Entire. Aspect: Slightly upright to horizontal; reflexing with subsequent development. Texture and luster, upper surface: Smooth, glabrous; velvety; matte. Texture and luster, lower surface: Smooth, glabrous; moderately velvety; mostly matte with venation, glossy. Color: When opening, upper surface: Close to 155C slightly tinged with close to 65D; towards the base, close to 2B. When opening, lower surface: Close to 62A and 62B; towards the apex, close to 155D; towards the base, close to 154C to 154D. Fully opened, upper surface: Close to 62B; towards the apex, close to 75C; towards the base, close to 13B to 13C; venation, similar to lamina; color becoming closer to 75C with subsequent development. Fully opened, lower surface: Close to 73C and 73D; towards the apex, close to 155C; towards the base, close to 13D; venation, close to N155A; color does not change with subsequent development.

*Disc florets*.—Quantity per inflorescence and arrangement: About 45 massed at the center of the inflorescence in about four spiral whorls; typically inconspicuous. Length: About 1.3 cm. Diameter: About 4 mm. Shape: Tubular, elongated; lower 85% fused and upper 15% free; apices, acute. Texture and luster, inner and outer surfaces: Smooth, glabrous; glossy. Color, when opening, inner and outer surfaces: Apex: Close to 13B. Mid-section: Close to 15A. Base: Close to 154C. Color, fully opened, inner and outer surfaces: Apex: Close to 13B. Mid-section and base: Close to 12A.

*Phyllaries*.—Quantity per inflorescence and arrangement: About eight in a single whorl. Length: About 1.5 cm. Width: About 7 mm. Shape: Oblanceolate. Apex: Acute. Base: Cuneate. Margin: Entire. Texture and luster, upper and lower surfaces: Smooth, glabrous; glossy. Color, upper surface: Close to NN137C. Color, lower surface: Close to NN137A.

*Peduncles*.—Length, terminal peduncle: About 9 cm. Diameter, terminal peduncle: About 3.5 mm. Strength: Strong. Aspect: Mostly upright. Texture and luster: Smooth, glabrous; moderately glossy. Color: Close to 146A.

*Reproductive organs*.—Androecium, present on disc florets only: Quantity per floret: About five. Filament length: About 4 mm. Filament color: Close to N155A. Anther size: About 4 mm by 0.5 mm. Anther shape: Narrowly oblong. Anther color: Close to 10A. Pollen amount: Moderate. Pollen color: Close to 17A. Gynoecium, present on disc florets only: Quantity per floret: One. Pistil length: About 9 mm. Style length: About 7 mm. Style color: Close to 154D. Stigma diameter: About 3 mm. Stigma shape: Cleft to three-parted. Stigma color: Close to 13A. Ovary color: Close to 145B. Seeds and fruits: To date, seed and fruit development have not been observed on plants of the new *Dahlia*.

Pathogen & pest resistance: To date, plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAMPI' as illustrated and described.

* * * * *